(12) United States Patent
Tratrat et al.

(10) Patent No.: US 11,866,412 B1
(45) Date of Patent: Jan. 9, 2024

(54) ACRIDIN-9-ONE COMPOUNDS AS ANTIBACTERIAL AGENTS

(71) Applicant: KING FAISAL UNIVERSITY, Al-Ahsa (SA)

(72) Inventors: Christophe Tratrat, Al-Ahsa (SA); Michelyne Haroun, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/116,920

(22) Filed: Mar. 3, 2023

(51) Int. Cl.
*C07D 219/06* (2006.01)
*C07D 471/04* (2006.01)

(52) U.S. Cl.
CPC ......... *C07D 219/06* (2013.01); *C07D 471/04* (2013.01)

(58) Field of Classification Search
CPC .............................. C07D 219/06; C07D 417/04
See application file for complete search history.

(56) References Cited

FOREIGN PATENT DOCUMENTS

| EP | 0471516 A1 | 8/1991 |
|---|---|---|
| JP | 2005500406 A | 1/2005 |

OTHER PUBLICATIONS

Salimon, et al. "Synthesis and pharmacological evaluation of 9(10H)-acridone bearing 1,3,4-oxadiazole derivatives as antimicrobial agents"; Arabian Journal of Chemistry; 2010.
Gensicka-Kowalewska, et al. "Recent developments in the synthesis and biological activity of acridine/acridone analogues"; RSC Advances; Mar. 4, 2017.
Rocchi, et al. "Sustainable Access to Acridin-9-(10H)ones with an Embedded m-Terphenyl Moiety Based on a Three-Component Reaction"; Molecules; Nov. 27, 2020.

*Primary Examiner* — D Margaret M Seaman
(74) *Attorney, Agent, or Firm* — Nath, Goldberg & Meyer; Richard C. Litman

(57) ABSTRACT

Novel acridin-9-one derivative compounds having broad spectrum antibacterial activity, a method of making said compounds, methods of using said compounds, and a pharmaceutical composition comprising said compound(s) are provided. The acridin-9-one compounds have antimicrobial activity against various susceptible and resistant gram-positive and gram-negative bacteria as well as drug resistant bacteria. They act as DNA gyrase and topoisomerase IV inhibitors and are satisfiable as a drug for infectious treatment.

18 Claims, No Drawings

ACRIDIN-9-ONE COMPOUNDS AS ANTIBACTERIAL AGENTS

BACKGROUND

1. Field

The disclosure of the present patent application relates to acridin-9-one derivatives as antibacterial agents.

2. Description of the Related Art

The infectious diseases caused by bacterial resistance to antibiotics constitute an increasing threat to humans on a global scale. An increasing number of infectious bacteria, including tuberculosis, pneumonia, salmonellosis, and gonorrhea, are becoming progressively challenging to cure owing to the ineffectiveness of currently used clinical antibiotics and present a serious health threat worldwide in the medical community. The major concern of this global health threat is the ability of the microorganisms to develop one or several mechanisms of resistance to antibiotics, rendering them inefficient for therapeutic treatment. The quest for discovering novel scaffolds with antimicrobial properties is particularly challenging in hospital and healthcare settings. The emergence of drug resistant bacteria calls for constant development of new antibacterial agents with the aim of generating medicaments that are potent against drug sensitive and resistant bacteria and well tolerated.

DNA gyrase and topoisomerase IV are attractive targets for developing antibacterial agents in order to combat the emerging bacterial resistance. Novobiocin, an aminocoumarin class, has been the only ATP-competitive inhibitor of these two enzymes used clinically but was withdrawn recently for toxicity concerns. The steady demand of generating novel DNA Gyrase B/topoisomerase IV inhibitors is paramount importance for infectious diseases treatment. New compounds demonstrating a broad spectrum of activity against infectious bacteria and diseases including gram positive and gram negative bacteria, tuberculosis mycobacteria, pneumonia, salmonellosis and gonorrhea among others, are desired, as well as such compounds demonstrating potent activity against drug resistant bacteria such as MRSA, VRSA.

A chosen molecular target of new compound derivatives was identified as DNA Gyrase B/topoisomerase IV which the above-mentioned novobiocin inhibited, albeit with adverse effects. Based on their pharmacological profiles, new compounds may find important clinical applications for severe infectious diseases including tuberculosis, among others.

The development of a compound(s) having a novel chemical structure different from that of known DNA gyrase and topoisomerase IV inhibitors and fully satisfiable as a drug for infectious treatment, as well as a pharmaceutical composition containing said compound as an active ingredient, is desired.

SUMMARY

The present subject matter relates to new compounds of acridin-9-one derivatives as antibacterial agents that have antimicrobial properties against various susceptible and resistant gram-positive and gram-negative bacteria as well as drug resistant bacteria. Also presented is a production synthesis method for said compounds, a pharmaceutical composition comprising the compound as an active ingredient, and methods of treatment using the present compounds. The compounds possess enzymatic activity and inhibition against DNA gyrase and topoisomerase IV enzymes as well as having antibacterial properties. The subject matter includes compounds of formula I, and a number of species compounds falling thereunder.

In one embodiment, the present subject matter may include acridin-9-one compound having the formula I:

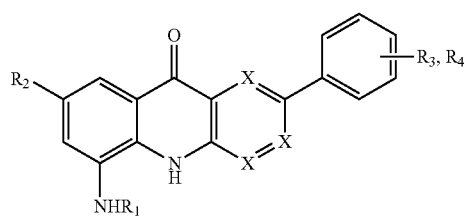

or a pharmaceutically acceptable salt, ester stereoisomer, or solvate thereof, wherein: each X is independently CH or nitrogen; $R_1$ is H, $C_1$-$C_6$ alkyl, or $C_3$-$C_8$ cycloalkyl; $R_2$ is H or a halogen; $R_3$ and $R_4$ may independently be the same or different and are of H, —$CO_2R$, —OR, —$CF_3$, —$OCF_3$, —$CH_2NR'R''$, —CONR'R'', —$CH_2CO_2R$, —$CH_2OH$, —$SO_2NHR$, or —$SO_2R$; and R, R', and R'' may each independently be H or $C_1$-$C_6$ alkyl. In another embodiment, the present subject matter relates to an acridin-9-one compound having the formula I:

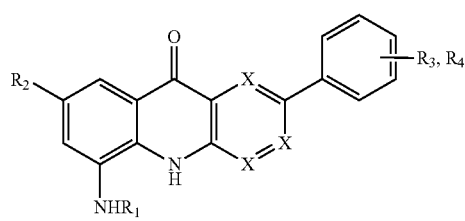

or a pharmaceutically acceptable salt, ester stereoisomer, or solvate thereof, wherein: each X is independently CH or nitrogen; $R_1$ is $CH_3$; $R_2$ is F; and $R_3$ and $R_4$ are independently H, —$CO_2H$, —OH, —$CF_3$, or —$CH_2N(CH_3)$ ($C_5H_{11}$).

In a further embodiment, the present subject matter relates to a compound selected from the group consisting of:

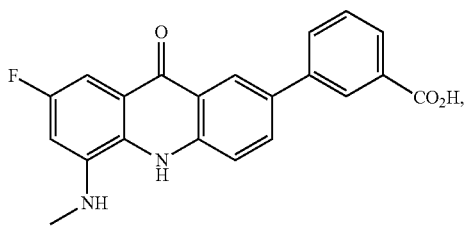

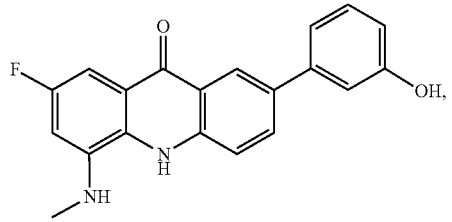

2

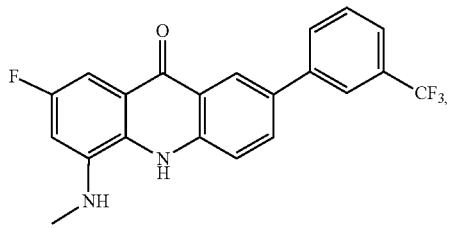

3

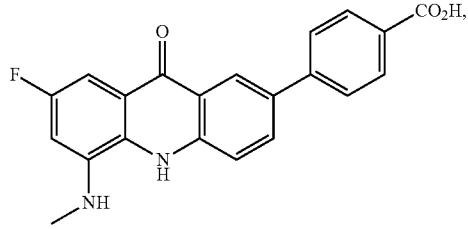

4

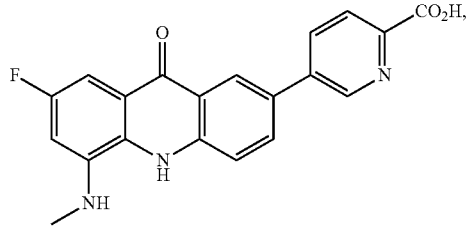

5

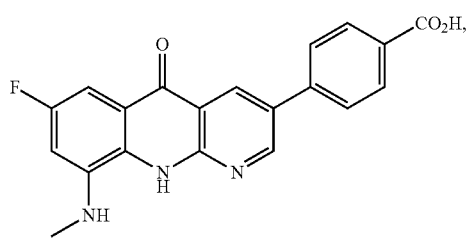

6

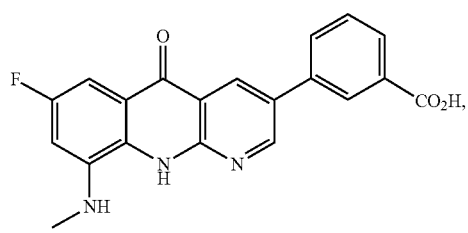

7

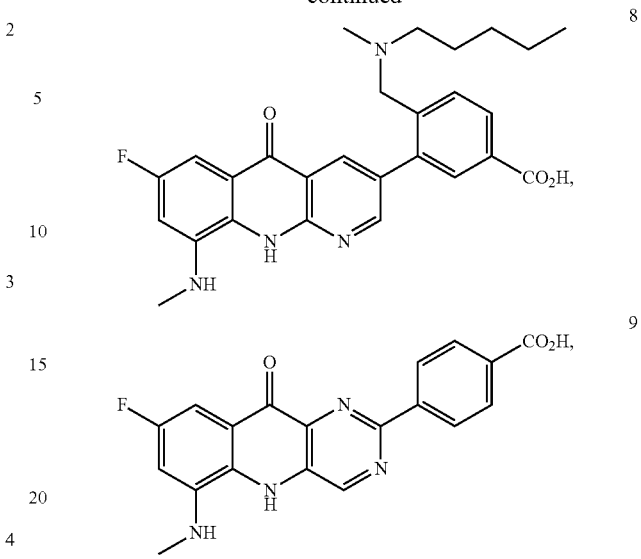

8

9 and a pharmaceutically acceptable salt, ester, stereoisomer, or solvate thereof. In an embodiment, the present subject matter relates to a process for the synthesis of the compounds of formula I, including a number of species or specific structures falling under structural formula I. —Further contemplated herein are pharmaceutical compositions containing these compounds, as well as methods of treating various bacterial infections by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group:. —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic arbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

Acridin-9-One Compounds:

In one embodiment, the present subject matter may include acridin-9-one compound having the formula I:

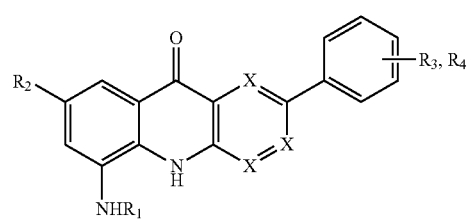

or a pharmaceutically acceptable salt, ester stereoisomer, or solvate thereof, wherein: each X is independently CH or nitrogen; $R_1$ is H, $C_1$-$C_6$ alkyl, or $C_3$-$C_8$ cycloalkyl; $R_2$ is H or a halogen; $R_3$ and $R_4$ may independently be the same or different and are of H, —$CO_2R$, —OR, —$CF_3$, —$OCF_3$, —$CH_2NR'R''$, —CONR'R'', —$CH_2CO_2R$, —$CH_2OH$, —$SO_2NHR$, or —$SO_2R$; and R, R', and R'' may each independently be H or $C_1$-$C_6$ alkyl. In another embodiment, the present subject matter relates to an acridin-9-one compound of formula I, wherein $R_1$ is $CH_3$; $R_2$ is F; and $R_3$ and $R_4$ are independently H, —CO2H, —OH, —CF3—CH2N(CH3)($C_5H_{11}$).

In a further embodiment, the present subject matter relates to an acridin-9-one compound of formula I, wherein one of $R_3$ and $R_4$ is H and the other is —$CO_2H$, —OH, or —$CF_3$.

In still another embodiment, the present subject matter relates to an acridin-9-one compound of formula I, wherein one of $R_3$ and $R_4$ is —$CO_2H$ and the other is —$CH_2N(CH_3)$($C_5H_{11}$).

In another embodiment, the present subject matter relates to an acridin-9-one compound having the formula I:

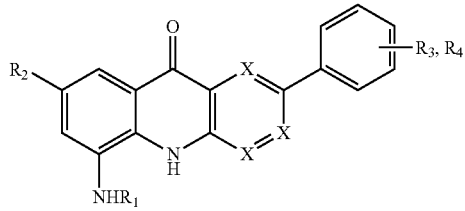

or a pharmaceutically acceptable salt, ester stereoisomer, or solvate thereof, wherein: each X is independently CH or nitrogen; $R_1$ is $CH_3$; $R_2$ is F; and $R_3$ and $R_4$ are independently H, —$CO_2H$, —OH, —$CF_3$, or —$CH_2N(CH_3)(C_5H_{11})$.

In a further embodiment, the present subject matter relates to a compound selected from the group consisting of:

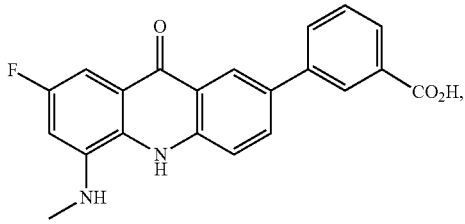

1

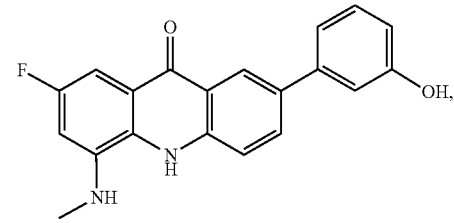

2

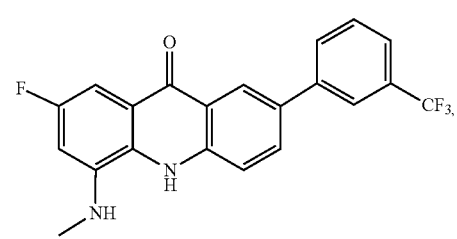

3

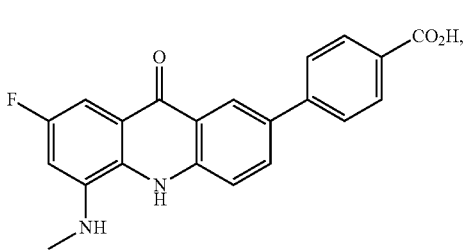

4

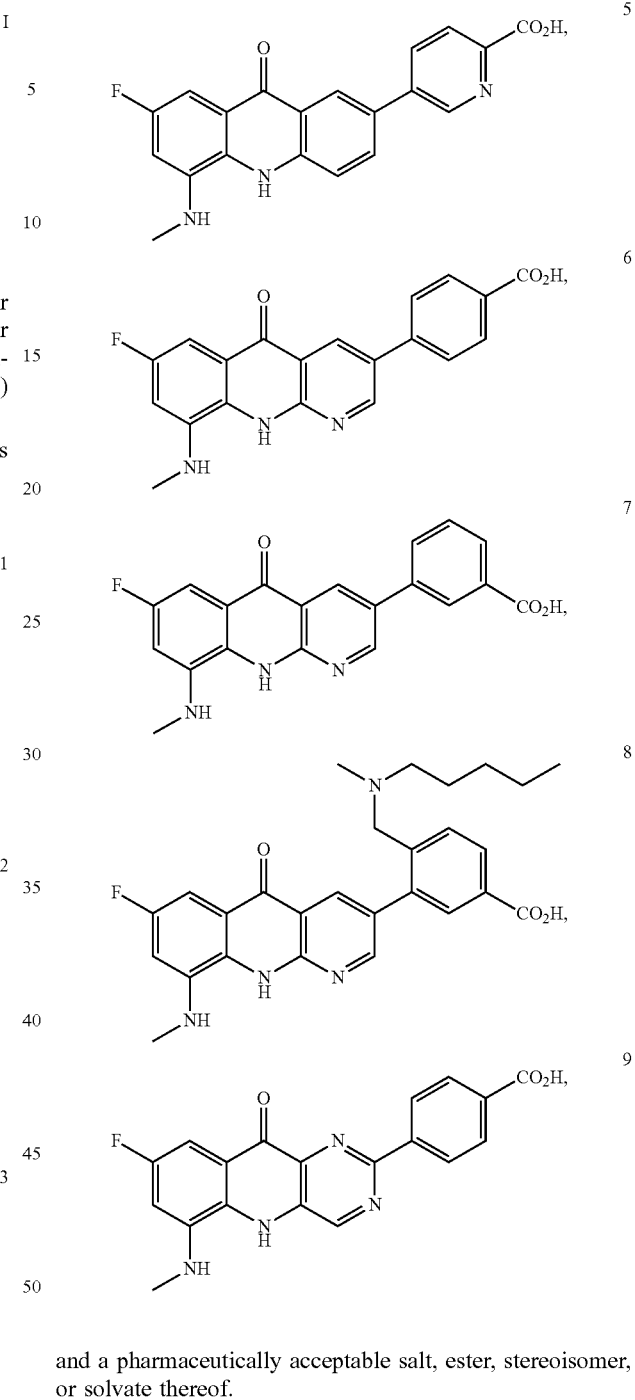

and a pharmaceutically acceptable salt, ester, stereoisomer, or solvate thereof.

It is to be understood that the present subject matter covers all combinations of substituent groups referred to herein.

In further embodiments, the acridin-9-one derivative compounds are shown to have promising antimicrobial activity against various susceptible and resistant gram-positive and gram-negative bacteria, and to possess enzymatic activity against DNA gyrase and topoisomerase IV enzymes as well as antibacterial properties.

In an embodiment of the present subject matter, acridin-9-one derivatives are illustrated by the group of the following compounds:

Example 1: 3-(7-fluoro-5-(methylamino)-9-oxo-9,10-dihydroacridin-2-yl)benzoic acid having the following structure:

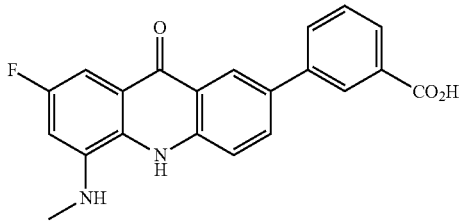

1

Example 2: 2-fluoro-7-(3-hydroxyphenyl)-4-(methylamino)acridin-9(10H)-one having the following structure:

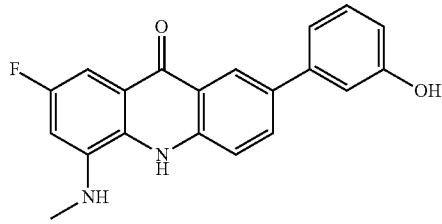

2

Example 3: 2-fluoro-4-(methylamino)-7-(3-(trifluoromethyl)phenyl)acridin-9(10H)-one having the following structure:

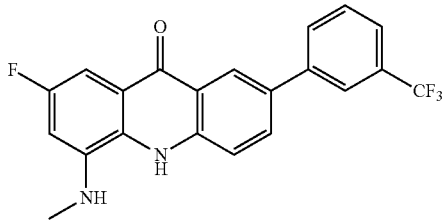

3

Example 4: 4-(7-fluoro-5-(methylamino)-9-oxo-9,10-dihydroacridin-2-yl)benzoic acid having the following structure:

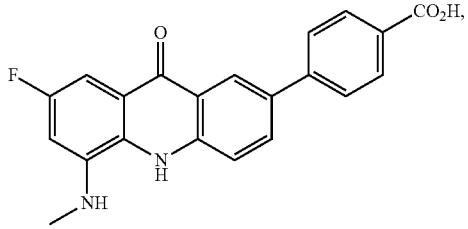

4

Example 5: 5-(7-fluoro-5-(methylamino)-9-oxo-9,10-dihydroacridin-2-yl)picolinic acid having the following structure:

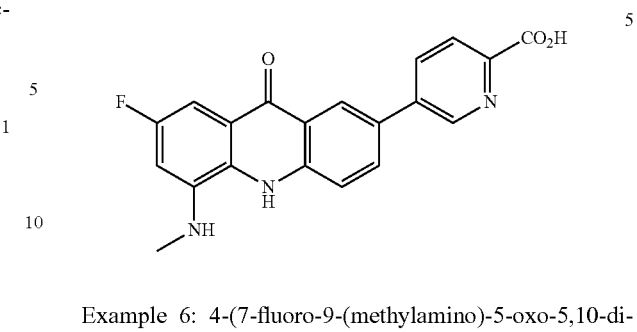

5

Example 6: 4-(7-fluoro-9-(methylamino)-5-oxo-5,10-dihydrobenzo[b][1,8]naphthyridin-3-yl)benzoic acid having the following structure:

6

Example 7: 3-(7-fluoro-9-(methylamino)-5-oxo-5,10-dihydrobenzo[b][1,8]naphthyridin-3-yl)benzoic acid having the following structure:

7

Example 8: 3-(7-fluoro-9-(methylamino)-5-oxo-5,10-dihydrobenzo[b][1,8]naphthyridin-3-yl)-4-((methyl(pentyl)amino)methyl)benzoic acid having the following structure:

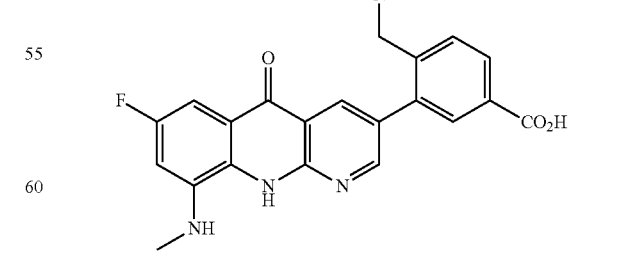

8

Example 9: 4-(8-fluoro-6-(methylamino)-10-oxo-5,10-dihydropyrimido[5,4-b]quinolin-2-yl)benzoic acid having the following structure:

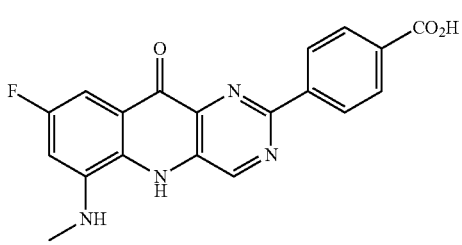 [SMILES: CNc1cc(F)cc2c(=O)c3cc(-c4ccc(C(=O)O)cc4)ccc3[nH]c12]

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

Synthesis:

In one embodiment, the present subject matter further relates to a process for synthesizing the acridin-9-one derivative compounds of formula I, the process comprising:

preparing a 2-((4-bromophenyl)amino)-5-fluoro-3-nitrobenzoic acid of the formula III:

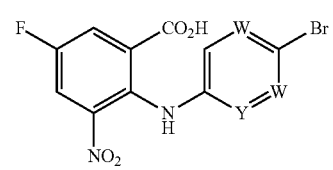

by reacting

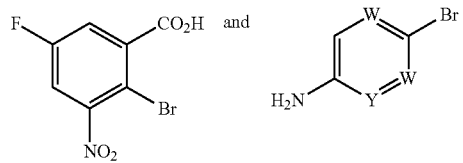

in the presence of K₂CO₃, wherein Y and W are each independently CH or N;

reacting the 2-((4-bromophenyl)amino)-5-fluoro-3-nitrobenzoic acid of the formula III with Eaton's reagent to obtain a 7-bromo-2-fluoro-4-nitroacridin-9(10H)-one of the formula IV:

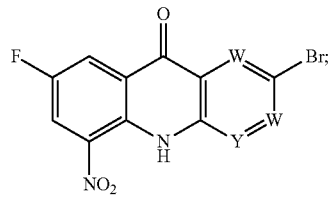

IVa: Y = CH, W = CH
IVb: Y = N, W = CH
IVc: Y = CH, W = N reacting the 7-bromo-2-fluoro-4-nitroacridin-9(10H)-one of the formula IV first with SnCl₂ in DMF, then with CH₃I in the presence of DMF to obtain an acridine derivative of the formula V:

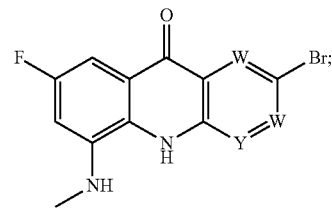

Va: Y = CH, W = CH
Vb: Y = N, W = CH
Vc: Y = CH, W = N and converting the acridine derivative of the formula V to produce the acridin-9-one compound of formula I.

Following are general synthetic schemes for each stage of the process

Preparation of 2-((4-bromophenyl)amino)-5-fluoro-3-nitrobenzoic acid IIIa

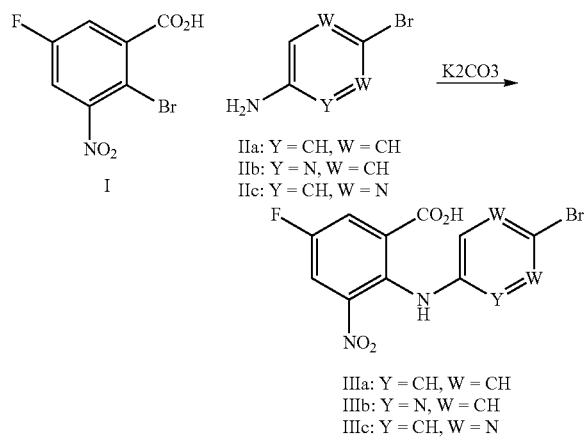

IIa: Y = CH, W = CH
IIb: Y = N, W = CH
IIc: Y = CH, W = N

IIIa: Y = CH, W = CH
IIIb: Y = N, W = CH
IIIc: Y = CH, W = N

Preparation of 7-bromo-2-fluoro-4-nitroacridin-9(10H)-one IVa

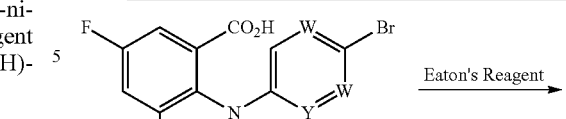

IIIa: Y = CH, W = CH
IIIb: Y = N, W = CH
IIIc: Y = CH, W = N

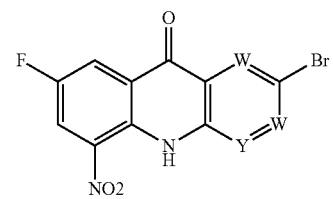

IVa: Y = CH, W = CH
IVb: Y = N, W = CH
IVc: Y = CH, W = N

Preparation of 7-bromo-fluoro-4-(methylamino)acridin-9(10H)-one Va

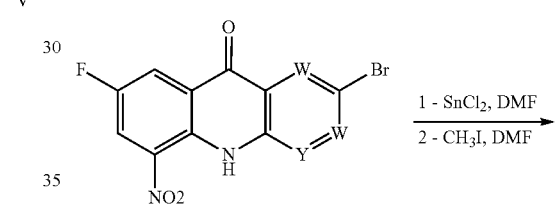

IVa: Y = CH, W = CH
IVb: Y = N, W = CH
IVc: Y = CH, W = N

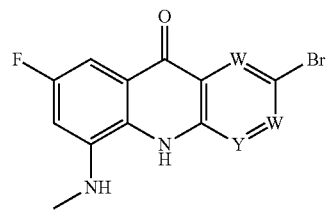

Va: Y = CH, W = CH
Vb: Y = N, W = CH
Vc: Y = CH, W = N

General preparation of the acridin-9-one derivatives (1)-(9)

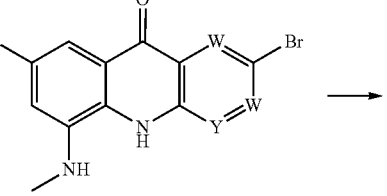

Va: Y = CH, W = CH
Vb: Y = N, W = CH
Vc: Y = CH, W = N

-continued

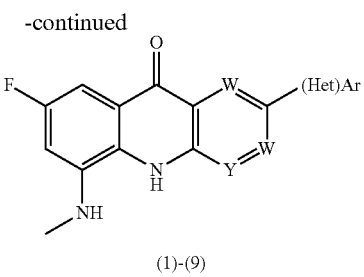

(1)-(9)

To a suspension of acridine derivative Va-c (1 mmol) in toluene (10 mL) were added Pd$_2$(dba)$_3$ (0.1 mmol), Xantphos (0.2 mmol) and Na$_2$CO$_3$ (3 mmol, 2 mL H$_2$O ) and arylboronic acid (1.5 mmol) and heated at reflux for 4h under argon atmosphere, and then concentrated under reduced pressure. The crude product was dissolved in ethyl acetate (20 mL), and washed with brine and water. The combined organic layers were dried over MgSO$_4$, then filtered and the solvent was removed under reduced pressure. The product was purified by flash chromatography or by crystallization to produce the expected acridin-9-one derivatives (1)-(9).

Pharmaceutical Compositions:

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for an acute or chronic airway disease or disorder. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of a bacterial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

Methods of Use:

The present compounds have valuable pharmaceutical properties, which make them commercially utilizable. Accordingly, the present subject matter further relates to use of the present compounds for the treatment of diseases or infections, especially bacterial infections and/or tuberculosis.

In this regard, the present subject matter relates to a method of treating a bacterial infection in a patient, comprising administering to a patient in need thereof a therapeutically effective amount of a compound as described herein.

In a further embodiment, the bacterial infection treatable herein can be caused by Gram-positive *Staphylococcus aureus, Staphylococcus aureus* resistant to MRSA, *Staphylococcus epidermidis, Bacillus subtilis, Enterococcus faecium, Enterococcus faecium* resistant to VRE, or Gram-negative organisms including *Klebsiella pneumonia, Escherichia coli*, or *Pseudomonas aeruginosa*, or any combination thereof.

In one specific embodiment, the bacterial infection can be caused by H37Rv type of M. tuberculosis strains. In another specific embodiment, the bacterial infection can be caused by *E. coli* DNA Gyrase.

The compounds as described herein are not only new but have very valuable antimicrobial properties. These compounds showed a broad spectrum of activity against gram positive and gram-negative bacteria, as well *tuberculosis mycobacteria*. They also showed potent activity against drug resistant bacteria such as MRSA and VRSA. The molecular target of these derivatives was identified as DNA Gyrase B. Based on their pharmacological profiles, the present compounds may find important clinical applications for severe infectious diseases and tuberculosis.

The present subject matter also relates to the use of a compound as described herein in the manufacture of a pharmaceutical composition for the treatment of bacterial infections, such as the diseases or disorders exemplified above. In particular, the present subject matter relates to the use of a compound as described herein in the manufacture of a pharmaceutical composition for the treatment or prophylaxis of bacterial infection, such as, but not limited to, bacterial infections caused by Gram-positive *Staphylococcus aureus, Staphylococcus aureus* resistant to MRSA, *Staphylococcus epidermidis, Bacillus subtilis, Enterococcus faecium, Enterococcus faecium* resistant to VRE, Gram-negative organisms including *Klebsiella pneumonia, Escherichia coli*, or *Pseudomonas aeruginosa*, H37Rv type of M. tuberculosis strains, *E. coli* DNA Gyrase, or any combination thereof.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In an embodiment, the present subject matter relates to a method of treating a bacterial infection caused by, for example, but not limited to, Gram-positive *Staphylococcus aureus, Staphylococcus aureus* resistant to MRSA, *Staphylococcus epidermidis, Bacillus subtilis, Enterococcus faecium, Enterococcus faecium* resistant to VRE, Gram-negative organisms including *Klebsiella pneumonia, Escherichia coli,* or *Pseudomonas aeruginosa,* H37Rv type of M. tuberculosis strains, *E. coli* DNA Gyrase, or any combination thereof comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used.

The following examples relate to various methods of manufacturing certain specific compounds as described herein.

EXAMPLES

Example 1

Preparation of
2-((4-bromophenyl)amino)-5-fluoro-3-nitrobenzoic acid IIIa

A mixture of 2-bromo-5-fluoro-3-nitrobenzoic acid I (5 mmol), 4-bromoaniline IIa (5.2 mmol), and potassium carbonate (5.2 mmol) in 15 mL dimethylformamide was heated at reflux for 12 h. After cooling to room temperature, the reaction mixture was diluted with 50 mL water and the resulting precipitate was filtered, washed with water and recrystallized to give the derivative IIIa. Elemental Analysis: Calculated C, 43.97; H, 2.27; N, 7.89; Found C, 43.91; H, 2.30; N, 7.93.

Example 2

Preparation of 2-((5-bromopyridin-2-yl)amino)-5-fluoro-3-nitrobenzoic acid IIb

Proceeding in a similar manner to the preparation of compound IIa, but using 2-amino-5-bromopyridine IIb instead of 4-bromoaniline IIa providing the derivative IIIb. Elemental Analysis: Calculated C, 40.47; H, 1.98; N, 11.80; Found C, 40.42; H, 2.03; N, 11.89.

Example 3

Preparation of 2-((2-bromopyrimidin-5-yl)amino)-5-fluoro-3-nitrobenzoic acid IIIc Proceeding in a similar manner to the preparation of compound IIIa, but using 5-amino-2-bromopyrimidine IIc instead of 4-bromoaniline IIa providing the derivative IIc. Elemental Analysis: Calculated C, 37.00; H, 1.69; N, 15.69; Found C, 36.93; H, 1.74; N, 15.32.

Example 4

Preparation of
7-bromo-2-fluoro-4-nitroacridin-9(10H)-one IVa

A mixture of 2-((4-bromophenyl)amino)-5-fluoro-3-nitrobenzoic acid IIIa (5 mmol) and Eaton's reagent (10 wt % phosphorus pentoxide solution in methanesulfonic acid) (5 mL) was heated at 90° C. for 2-3 h. After cooling to room temperature, the reaction mixture was transferred to an excess saturated sodium carbonate solution (100 mL). The solid obtained was filtered, washed and recrystallized to provide the corresponding acridinone Iva. Elemental Analysis: Calculated C, 46.32; H, 1.79; N, 8.31; Found C, 46.27; H, 1.82; N, 8.26.

Example 5

Preparation of 3-bromo-7-fluoro-9-nitrobenzo[b][1,8]naphthyridin-5(10H)-one IVb

Proceeding in a similar manner to the preparation of compound Iva, but using 2-((5-bromopyridin-2- yl)amino)-5-fluoro-3-nitrobenzoic acid IIIb instead of 2-((4-bromophenyl)amino)-5-fluoro-3-nitrobenzoic acid IIIa providing the derivative IVb. Elemental Analysis: Calculated C, 42.63; H, 1.49; N, 12.43; Found C, 42.70; H, 1.53; N, 12.37.

Example 6

Preparation of 2-bromo-8-fluoro-6-nitropyrimido[5,4-b]quinolin-10(5H)-one IVc

Proceeding in a similar manner to the preparation of compound Iva, but using 2-((2-bromopyrimidin-5-yl)amino)-5-fluoro-3-nitrobenzoic acid IIIc instead of 2-((4-bromophenyl)amino)-5-fluoro-3-nitrobenzoic acid IIIa providing the derivative Ivc. Elemental Analysis: Calculated C, 38.96; H, 1.19; N, 16.52; Found C, 39.01; H, 1.16; N, 16.48.

Example 7

Preparation of 7-bromo-2-fluoro-4-(methylamino)acridin-9(10H)-one Va

To a solution of 7-bromo-2-fluoro-4-nitroacridin-9(10H)-one IVa (4 mmol) in 25 mL Dimethylformamide (DMF) was added $SnCl_2$, $2H_2O$ (24 mmol) and the reaction mixture was heated at 70° C. for 2 h. After cooling to room temperature, the mixture was concentrated and dissolved in ethyl acetate (EtOAc) (50 mL), washed with saturated aqueous $NaHCO_3$ and brine, dried with $MgSO_4$, and evaporated to provide the corresponding 4-aminoacridinone derivative which was engaged in the next step without further purification. To a solution of 4-aminoacridinone derivative (3 mmol) in 10 mL DMF were added $Na_2CO_3$ (1.5 mmol) and $CH_3I$ (3 mmol) dropwise. The reaction mixture was stirred at room temperature for 18 h. The reaction mixture was concentrated and purified by column chromatography to afford 7-bromo-2-fluoro-4-(methylamino)acridin-9(10H)-one Va. Elemental Analysis: Calculated C, 52.36; H, 3.14; N, 8.72; Found C, 52.33; H, 3.15; N, 8.68.

Example 8

Preparation of 3-bromo-7-fluoro-9-(methylamino)benzo[b][1,8]naphthyridin-5(10H)-one Vb Proceeding in a similar manner to the preparation of 7-bromo-2-fluoro-4-(methylamino)acridin-9(10H)-one Va, but using 3-bromo-7-fluoro-9-nitrobenzo[b][1,8]naphthyridin-5(10H)-one IVb instead of 7-bromo- 2-fluoro-4-nitroacridin-9(10H)-one IVa providing the derivative Vb. Elemental Analysis: Calculated C, 48.47; H, 2.82; N, 13.04; Found C, 48.51; H, 2.80; N, 12.99.

Example 9

Preparation of 2-bromo-8-fluoro-6-(methylamino) pyrimido[5,4-b]quinolin-10(5H)-one Vc:

Proceeding in a similar manner to the preparation of 7-bromo-2-fluoro-4-(methylamino)acridin-9(10H)-one Va, but using 2-bromo-8-fluoro-6-nitropyrimido [5,4-b]quinolin-10(5H)-one IVc instead of 7-bromo- 2-fluoro-4-nitroacridin-9(10H)-one IVa providing the derivative Vc. Elemental Analysis: Calculated C, 44.61; H, 2.50; N, 17.34; Found C, 44.57; H, 2.48; N, 17.30.

Example 10

3-(7-fluoro-5-(methylamino)-9-oxo-9,10-dihydroacridin-2-yl)benzoic acid (1)

The expected product was obtained in accordance with the general preparation of the derivatives (1)-(9) using 7-bromo-2-fluoro-4-(methylamino)acridin-9(10H)-one Va and 3-carboxyphenylboronic acid Elemental Analysis: Calculated C, 69.61; H, 4.17; N, 7.73; Found C, 69.58; H, 4.21; N, 7.80.

Example 11

2-fluoro-7-(3-hydroxyphenyl)-4-(methylamino)acridin-9(10H)-one (2)

The expected product was obtained in accordance with the general preparation of the derivatives (1)-(9) using 7-bromo-2-fluoro-4-(methylamino)acridin-9(10H)-one Va and 3-hydroxyphenylboronic acid. Elemental Analysis: Calculated C, 71.85; H, 4.52; N, 8.38; Found C, 71.92; H, 4.48; N, 8.41.

Example 12

2-fluoro-4-(methylamino)-7-(3-(trifluoromethyl) phenyl)acridin-9(10H)-one (3)

The expected product was obtained in accordance with the general preparation of the derivatives (1)-(9) using 7-bromo-2-fluoro-4-(methylamino)acridin-9(10H)-one Va and 3-trifluoromethylphenylboronic acid. Elemental Analysis: Calculated C, 65.29; H, 3.65; N, 7.25; Found C, 65.32; H, 3.69; N, 7.23.

Example 13

4-(7-fluoro-5-(methylamino)-9-oxo-9,10-dihydroacridin-2-yl)benzoic acid (4)

The expected product was obtained in accordance with the general preparation of the derivatives (1)-(9) using 7-bromo-2-fluoro-4-(methylamino)acridin-9(10H)-one Va and 4-carboxyphenylboronic acid Elemental Analysis: Calculated C, 69.61; H, 4.17; N, 7.73; Found C, 69.56; H, 4.19; N, 7.69.

Example 14

5-(7-fluoro-5-(methylamino)-9-oxo-9,10-dihydroacridin-2-yl)picolinic acid (5)

The expected product was obtained in accordance with the general preparation of the derivatives (1)-(9) using 7-bromo-2-fluoro-4-(methylamino)acridin-9(10H)-one Va and 5-boronopicolinic acid Elemental Analysis: Calculated C, 66.11; H, 3.88; N, 11.56; Found C, 66.08; H, 3.86; N, 11.51.

Example 15

4-(7-fluoro-9-(methylamino)-5-oxo-5,10-dihydrobenzo[b][1,8]naphthyridin-3-yl)benzoic acid (6)

The expected product was obtained in accordance with the general preparation of the derivatives (1)-(9) using 3-bromo-7-fluoro-9-(methylamino)benzo[b][1,8]naphthyridin-5(10H)-one Vb and 4-carboxyphenylboronic acid. Elemental Analysis: Calculated C, 66.11; H, 3.88; N, 11.56; Found C, 66.07; H, 3.92; N, 11.61.

Example 16

3-(7-fluoro-9-(methylamino)-5-oxo-5,10-dihydrobenzo[b][1,8]naphthyridin-3-yl)benzoic acid (7)

The expected product was obtained in accordance with the general preparation of the derivatives (1)-(9) using 3-bromo-7-fluoro-9-(methylamino)benzo[b][1,8]naphthyridin-5(10H)-one Vb and 3-carboxyphenylboronic acid. Elemental Analysis: Calculated C, 66.11; H, 3.88; N, 11.56; Found C, 66.10; H, 3.93; N, 11.54.

Example 17

3-(7-fluoro-9-(methylamino)-5-oxo-5,10-dihydrobenzo[b][1,8]naphthyridin-3-yl)-4-((methyl(pentyl)amino)methyl)benzoic acid (8)

The expected product was obtained in accordance with the general preparation of the derivatives (1)-(9) using 3-bromo-7-fluoro-9-(methylamino)benzo[b][1,8]naphthyridin-5(10H)-one Vb and 3-borono-4-((methyl(pentyl)amino) methyl)benzoic acid. Elemental Analysis: Calculated C, 68.05; H, 6.13; N, 11.76; Found C, 68.11; H, 6.12; N, 11.80.

Example 18

4-(8-fluoro-6-(methylamino)-10-oxo-5,10-dihydropyrimido[5,4-b]quinolin-2-yl)benzoic acid (9)

The expected product was obtained in accordance with the general preparation of the derivatives (1)-(9) using 2-bromo-8-fluoro-6-(methylamino)pyrimido[5,4-13]quinolin-10(5H)-one Vc and 4-carboxyphenylboronic acid. Elemental Analysis: Calculated C, 62.64; H, 3.60; N, 15.38; Found C, 62.59; H, 3.64; N, 15.36.

Antibacterial Activity Evaluation

The following example relates to the antibacterial effectiveness of certain specific compounds as described herein.
Compounds 1-9 as identified above were evaluated for in vitro antibacterial activity according to the reported procedure (*Methods for Dilution Antimicrobial Susceptibility Tests for Bacteria That Grow Aerobically; Approved Standard—Tenth Edition*. CLSI document M07-A10. Wayne. PA: Clinical and Laboratory Standards Institute. 2015) against bacterial strains comprising Gram-positive *Staphylococcus aureus*, *Staphylococcus aureus* resistant to MRSA, *Staphylococcus epidermidis*, *Bacillus subtilis*, *Enterococcus faecium*, *Enterococcus faecium resistant* to VRE, and Gram-negative organisms including *Klebsiella pneumonia*, *Escherichia coli*, and *Pseudomonas aeruginosa*.

The biological results demonstrated that the present compounds possess favorable antimicrobial activity. By way of example, the compound of Example 17 (compound 8) displayed promising antibacterial activity against various drug sensitive and drug resistant bacterial strains as reported in Table 1.

TABLE 1

Antibacterial activity of compound 8

| Microorganisms | MIC µg/mL | | |
| --- | --- | --- | --- |
| | Compound 8 | Ciprofloxacin | Vancomycin |
| *Staphylococcus aureus* ATCC 29213 | 0.75 | 0.5 | 1 |
| *Staphylococcus aureus* ATCC BAA-1556 (MERSA resistant) | 0.75 | 16 | 1 |
| *Staphylococcus epidermidis* | 1 | 0.25 | 1 |
| *Bacillus subtilis* MTCC 441 | 0.5 | 0.25 | 0.5 |
| *Enterococcus faecium* ATCC 35667 | 0.1 | 4 | 0.5 |
| *Enterococcus faecium* ATCC 51559 (VRE resistant) | 0.1 | 16 | >128 |
| *Klebsiella pneumonia* MTCC 618 | 0.75 | 0.75 | >128 |
| *Escherichia coli* MTCC 443 | 2 | 0.05 | >128 |
| *Pseudomonas aeruginosa* MTCC 741 | 0.5 | 0.75 | >128 |

The antitubercular property of the compounds 1-9 was evaluated towards H37Rv type of M. tuberculosis strains. The inoculum was prepared from fresh Lowenstein-Jensen re-suspended in 7H9-5 medium (7H9 broth, 0.5% glycerol, 0.1% casitone, supplemented with oleic acid/albumin/dextrose/catalase (OADC), adjusted to a McFarland tube No. 1 and further diluted using sterile saline 1:20; 100 µL was used as inoculums. Each drug stock solution was thawed and diluted in 7H9-S at fourfold the final highest concentration assessed. Using one hundred microliter volume of 7H9-S broth, serial two-fold dilution was prepared of each drug directly in a sterile 96-well micro-titer plate. On each microplate, a growth control that does not contain antibiotic and composed of a sterile control were also effectuated. As water and media commonly evaporate from the closest wells to the plate perimeter during culture, sterile water was added to the perimeters of the wells to prevent evaporation during the incubation. The plate was covered then sealed in plastic bag and incubated at a temperature of 37° C. in normal atmosphere. After seven days of incubation, alamar blue solution (30 mL) was added to each well and the plate was re-incubated overnight. We added 50 µL of alamar blue having 0.25 µM concentration. A change in color from blue (oxidized state) to pink (reduced) indicated the growth of bacteria and MIC was defined as the lowest concentration of drug that prevented this change in color.

The biological results demonstrated that the present compounds possess favorable anti-mycobacterial activity. By way of example, compound 8 displayed a promising anti-mycobacterial activity of 4 micrograms/mL against mycobacterium tuberculosis H37Rv strain.

Example 20

Evaluation of Inhibitory Activities on *E. coli* DNA Gyrase.

Inhibitory potencies were investigated utilizing Inspiralis assay on streptavidin-coated 96-well microtiter plates. First, the plates were rehydrated with buffer (20 mM Tris-HCl with pH 7.6, 0.01% w/v BSA, 0.05% v/v Tween 20, 137 mM NaCl) and the biotinylated oligonucleotide was then immobilized. After washing off the unbound oligonucleotide, the enzyme test was performed. The reaction volume of 30 µL in buffer (35 mM Tris×HCl with pH 7.5, 4 mM MgCl2, 24 mM KCl, 2 mM DTT, 1.8 mM spermidine, 1 mM ATP, 6.5% w/v glycerol, 0.1 mg/mL albumin) contained 1.5 U of DNA gyrase from *E. coli*, 0.75 µg of relaxed pNO1 plasmid, and 3 µL solution of the inhibitor in 10% DMSO and 0.008% Tween 20. Reaction solutions were incubated at 37° C. for 30 min. After that, the TF buffer (50 mM NaOAc with pH 5.0, 50 mM NaCl and 50 mM MgCl2) was added to terminate the enzymatic reaction. After additional incubation for 30 min at rt, during which biotinoligonucleotide-plasmid triplex was formed, the unbound plasmid was washed off using TF buffer and SybrGOLD in T10 buffer (10 mM Tris HCl with pH 8.0 and 1 mM EDTA) was added. The fluorescence was measured with a microplate reader (BioTek Synergy H4, excitation: 485 nm, emission: 535 nm). Initial screening was done at 100 or 10 µM concentration of inhibitors. For the most active inhibitors IC50 was determined using seven concentrations of tested compounds. GraphPad Prism software was used to calculate the IC50 values. The result is given as the average value of three independent measurements. Novobiocin was used as a positive control.

The biological results demonstrated that the present compounds possessed favorable DNA Gyrase activity. By way of example, compound 8 displayed promising *E. coli* DNA Gyrase of 11 nM. In the same experimental condition, the reference control Novabiocin inhibited *E. coli* DNA Gyrase activity of 150 nM.

It is to be understood that the acridin-9-one derivative compounds as antibacterial agents are not limited to the specific embodiments or examples described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. An acridin-9-one compound having the formula I:

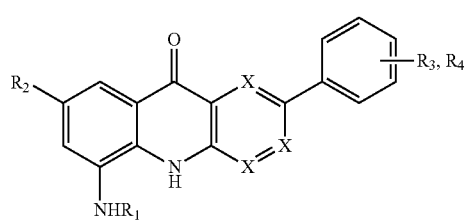

or a pharmaceutically acceptable salt, ester stereoisomer, or solvate thereof, wherein:
each X is independently CH or nitrogen;
$R_1$ is H, $C_1$-$C_6$ alkyl, or $C_3$-$C_8$ cycloalkyl;
$R_2$ is H or a halogen;
$R_3$ and $R_4$ may independently be the same or different and are of H, —$CO_2R$, —OR, —$CF_3$, —$OCF_3$, —$CH_2NR'R''$, —$CONR'R''$, —$CH_2CO_2R$, —$CH_2OH$, —$SO_2NHR$, or —$SO_2R$; and
R, R', and R'' may each independently be H or $C_1$-$C_6$ alkyl.

2. The acridin-9-one compound of claim 1, wherein $R_1$ is $CH_3$; $R_2$ is F; and $R_3$ and $R_4$ are independently H, —$CO_2H$, —OH, —$CF_3$— $CH_2N(CH_3)(C_5H_{11})$.

3. The acridin-9-one compound of claim 1, wherein one of $R_3$ and $R_4$ is H and the other is —$CO_2H$, —OH, —$CF_3$.

4. The acridin-9-one compound of claim 1, wherein one of $R_3$ and $R_4$ is —$CO_2H$ and the other is —$CH_2N(CH_3)(C_5H_{11})$.

5. A pharmaceutically acceptable composition comprising a therapeutically effective amount of the compound of claim 1 and a pharmaceutically acceptable carrier.

6. A method of treating a bacterial infection in a patient, comprising administering to a patient in need thereof a therapeutically effective amount of the compound of claim 1.

7. The method of claim 6, wherein the bacterial infection is caused by Gram-positive *Staphylococcus aureus, Staphylococcus aureus* resistant to MRSA, *Staphylococcus epidermidis, Bacillus subtilis, Enterococcus faecium, Enterococcus faecium* resistant to VRE, or Gram-negative organisms including *Klebsiella pneumonia, Escherichia coli,* or *Pseudomonas aeruginosa*.

8. The method of claim 6, wherein the bacterial infection is caused by H37Rv type of M. tuberculosis strains.

9. The method of claim 6, wherein the bacterial infection is caused by *E. coli* DNA Gyrase.

10. A process for synthesizing the acridin-9-one derivative compounds of claim 1, the process comprising:
preparing a 2-((4-bromophenypamino)-5-fluoro-3-nitrobenzoic acid of the formula III:

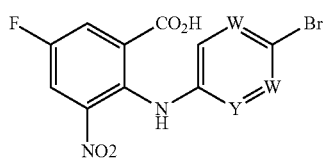

by reacting

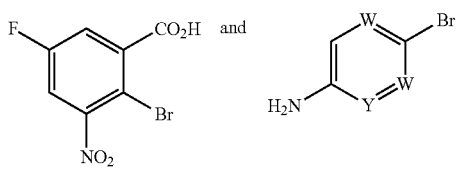

in the presence of $K_2CO_3$, wherein Y and W are each independently CH or N;
reacting the 2-((4-bromophenyl)amino)-5-fluoro-3-nitrobenzoic acid of the formula III with Eaton's reagent to obtain a 7-bromo-2-fluoro-4-nitroacridin-9(10H)-one of the formula IV:

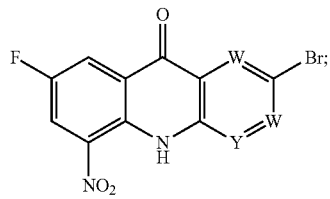

IVa: Y = CH, W = CH
IVb: Y = N, W = CH
IVc: Y = CH, W = N reacting the 7-bromo-2-fluoro-4-nitroacridin-9(10H)-one of the formula IV first with $SnCl_2$ in DMF, then with $CH_3I$ in the presence of DMF to obtain an acridine derivative of the formula V:

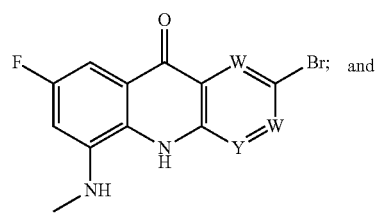

Va: Y = CH, W = CH
Vb: Y = N, W = CH
Vc: Y = CH, W = N converting the acridine derivative of the formula V to produce the acridin-9-one compound of formula I.

11. An acridin-9-one compound having the formula I:

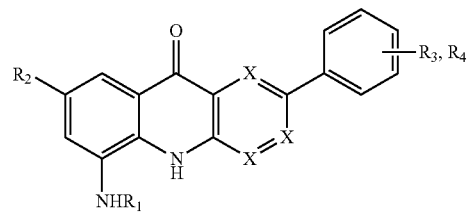

or a pharmaceutically acceptable salt, ester stereoisomer, or solvate thereof, wherein:
each X is independently CH or nitrogen;
$R_1$ is $CH_3$;
$R_2$ is F; and
$R_3$ and $R_4$ are independently H, —$CO_2H$, —OH, —$CF_3$, or —$CH_2N(CH_3)(C_5H_{11})$.

12. The acridin-9-one compound of claim 11, wherein one of $R_3$ and $R_4$ is H and the other is —$CO_2H$, —OH, —$CF_3$.

13. The acridin-9-one compound of claim 11, wherein one of $R_3$ and $R_4$ is —$CO_2H$ and the other is —$CH_2N(CH_3)(C_5H_{11})$.

14. A pharmaceutically acceptable composition comprising a therapeutically effective amount of the compound of claim 11 and a pharmaceutically acceptable carrier.

15. A method of treating a bacterial infection in a patient, comprising administering to a patient in need thereof a therapeutically effective amount of the compound of claim 11.

16. An acridin-9-one compound selected from the group consisting of:

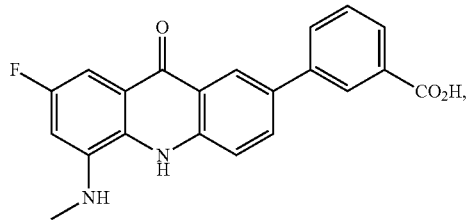
1

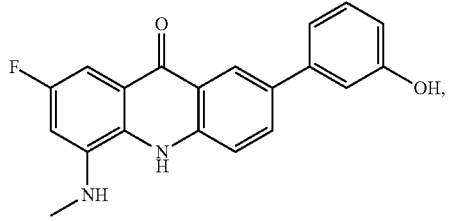
2

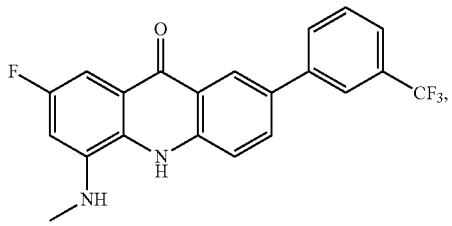
3

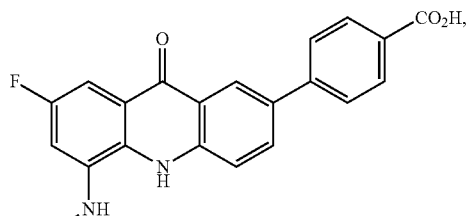
4

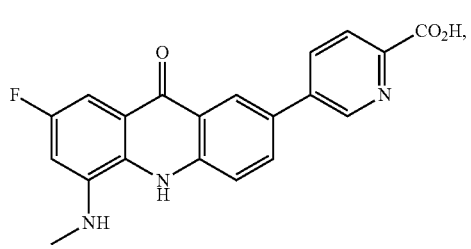
5

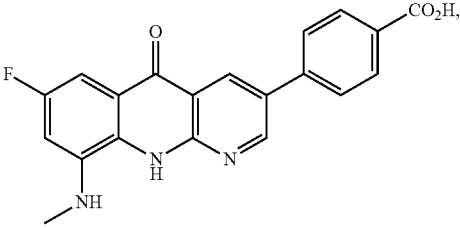
6

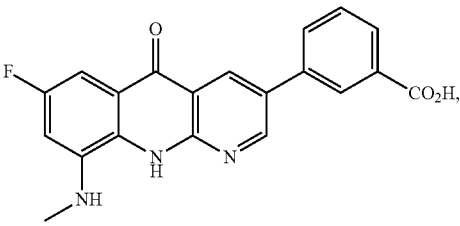
7

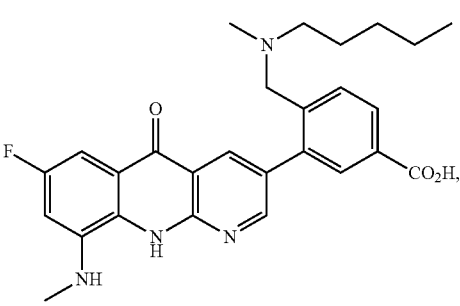
8

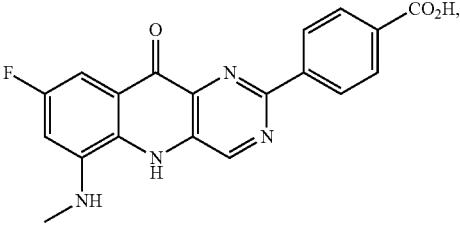
9 and a pharmaceutically acceptable salt, ester, stereoisomer, or solvate thereof.

17. A pharmaceutically acceptable composition comprising a therapeutically effective amount of the compound of claim 16 and a pharmaceutically acceptable carrier.

18. A method of treating a bacterial infection in a patient, comprising administering to a patient in need thereof a therapeutically effective amount of the compound of claim 16.

* * * * *